(12) United States Patent
Starr et al.

(10) Patent No.: US 9,927,354 B1
(45) Date of Patent: Mar. 27, 2018

(54) METHOD AND APPARATUS FOR PIPE IMAGING WITH CHEMICAL ANALYSIS

(71) Applicant: RedZone Robotics, Inc., Pittsburgh, PA (US)

(72) Inventors: Justin Starr, Baden, PA (US); John Lettman, Pittsburgh, PA (US); Todd Kueny, Tarentum, PA (US); Foster J. Salotti, Verona, PA (US); Galin Konakchiev, Pittsburgh, PA (US)

(73) Assignee: RedZone Robotics, Inc., Pittsburgh, PA (US)

( * ) Notice: Subject to any disclaimer, the term of this patent is extended or adjusted under 35 U.S.C. 154(b) by 0 days.

(21) Appl. No.: 15/278,879

(22) Filed: Sep. 28, 2016

(51) Int. Cl.
| | |
|---|---|
| *G01N 21/35* | (2014.01) |
| *G01N 21/954* | (2006.01) |
| *G01N 21/94* | (2006.01) |
| *B25J 5/00* | (2006.01) |
| *F16L 55/32* | (2006.01) |
| *G01N 21/3581* | (2014.01) |
| *F16L 101/30* | (2006.01) |
| *G01S 13/88* | (2006.01) |
| *G01S 15/88* | (2006.01) |
| *G01S 17/88* | (2006.01) |

(52) U.S. Cl.
CPC .......... *G01N 21/3581* (2013.01); *B25J 5/005* (2013.01); *F16L 55/32* (2013.01); *G01N 21/94* (2013.01); *G01N 21/954* (2013.01); *F16L 2101/30* (2013.01); *G01N 2201/06113* (2013.01); *G01N 2201/12* (2013.01); *G01S 13/88* (2013.01); *G01S 15/88* (2013.01); *G01S 17/88* (2013.01); *Y10S 901/01* (2013.01); *Y10S 901/44* (2013.01)

(58) Field of Classification Search
CPC .. F16L 2101/30; F16L 55/32; G01N 21/3581; G01N 21/94; G01N 21/954; G01N 2201/06113; G01N 2201/12; G01S 13/88; G01S 15/88; G01S 17/88; Y10S 901/01; Y10S 901/44
See application file for complete search history.

(56) References Cited

U.S. PATENT DOCUMENTS

| | | | | |
|---|---|---|---|---|
| 8,567,536 | B1 * | 10/2013 | Canfield | B62D 55/075 |
| | | | | 180/9.21 |
| 8,767,912 | B1 * | 7/2014 | Alzaidi | G01B 15/02 |
| | | | | 250/268 |
| 9,244,024 | B1 * | 1/2016 | Patterson | G01N 23/18 |
| 2008/0105067 | A1 * | 5/2008 | Frey | G01B 11/24 |
| | | | | 73/865.8 |
| 2008/0194969 | A1 * | 8/2008 | Werahera | A61B 5/0059 |
| | | | | 600/476 |
| 2011/0168900 | A1 * | 7/2011 | Dobbs | G01B 15/02 |
| | | | | 250/360.1 |

(Continued)

*Primary Examiner* — Mark R Gaworecki
(74) *Attorney, Agent, or Firm* — Cafardi, Ferguson, Wyrick, Weis + Stotler, LLC; Andrew M. Gabriel

(57) ABSTRACT

One embodiment provides a method for identifying a target object of a pipe wall, including: positioning a pipe inspection robot within a pipe; emitting, using a terahertz (THz) beam source of the pipe inspection robot, a laser beam towards a target object; receiving, using a THz receiver of the pipe inspection robot, THz data related to the target object; analyzing, using a processor, the THz data; and determining, based on the analyzing, an identity of the object. Other aspects are described and claimed.

20 Claims, 3 Drawing Sheets

(56) References Cited

U.S. PATENT DOCUMENTS

| | | | |
|---|---|---|---|
| 2012/0044479 A1* | 2/2012 | Roulston | G01J 3/108 356/51 |
| 2012/0152877 A1* | 6/2012 | Tadayon | B25J 5/02 212/224 |
| 2013/0161514 A1* | 6/2013 | Kukushkin | G01N 21/3586 250/332 |
| 2014/0172374 A1* | 6/2014 | Brady | G01N 21/3581 702/189 |
| 2015/0146216 A1* | 5/2015 | Krauhausen | B21C 51/00 356/612 |
| 2015/0153234 A1* | 6/2015 | Kozlov | G01J 5/0803 250/341.1 |
| 2016/0039483 A1* | 2/2016 | Nielsen | B62D 55/075 180/164 |

* cited by examiner

US 9,927,354 B1

METHOD AND APPARATUS FOR PIPE IMAGING WITH CHEMICAL ANALYSIS

BACKGROUND

Pipes that carry water, other fluids and gases are an important type of infrastructure. Pipes are often inspected as a matter of routine upkeep or in response to a noticed issue. A great deal of pipe data is captured in still images or video, e.g., using cameras to record information from the visible spectrum of light. However, other data can provide additional information beyond what is visible to the naked eye. For example, acoustic, ultraviolet (UV) and infrared (IR) imaging have been utilized to identify details related to pipe topology or condition.

When inspecting pipes, experienced inspectors may observe a certain type of buildup, inflow of material, or defect and be able to produce a logical guess as to its composition or source, e.g., based upon the visual characteristics of that build-up. However, these guesses are not always accurate and are even more difficult to make if the substance to be identified is a liquid.

BRIEF SUMMARY

In summary, one aspect provides a pipe inspection robot, comprising: a powered track system providing movement to the pipe inspection robot; a sensor component; and a processor; said sensor component comprising a terahertz (THz) beam source and a receiver; said processor configured to: operate the sensor component to collect THz data related to a pipe wall; and communicate the THz data collected over a network connection.

Another aspect provides a system, comprising: a computing system; a pipe inspection robot operatively coupled to the computing system and comprising: a sensor portion; and a processor; said sensor component comprising a terahertz (THz) beam source and a receiver; said processor configured to: operate the sensor component to collect THz data related to a pipe wall; and communicate the THz data collected over a network connection to the computing system.

A further aspect provides a method for identifying a target object of a pipe wall, comprising: positioning a pipe inspection robot within a pipe; emitting, using a terahertz (THz) beam source of the pipe inspection robot, a laser beam towards a target object; receiving, using a THz receiver of the pipe inspection robot, THz data related to the target object; analyzing, using a processor, the THz data; and determining, based on the analyzing, an identity of the object.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
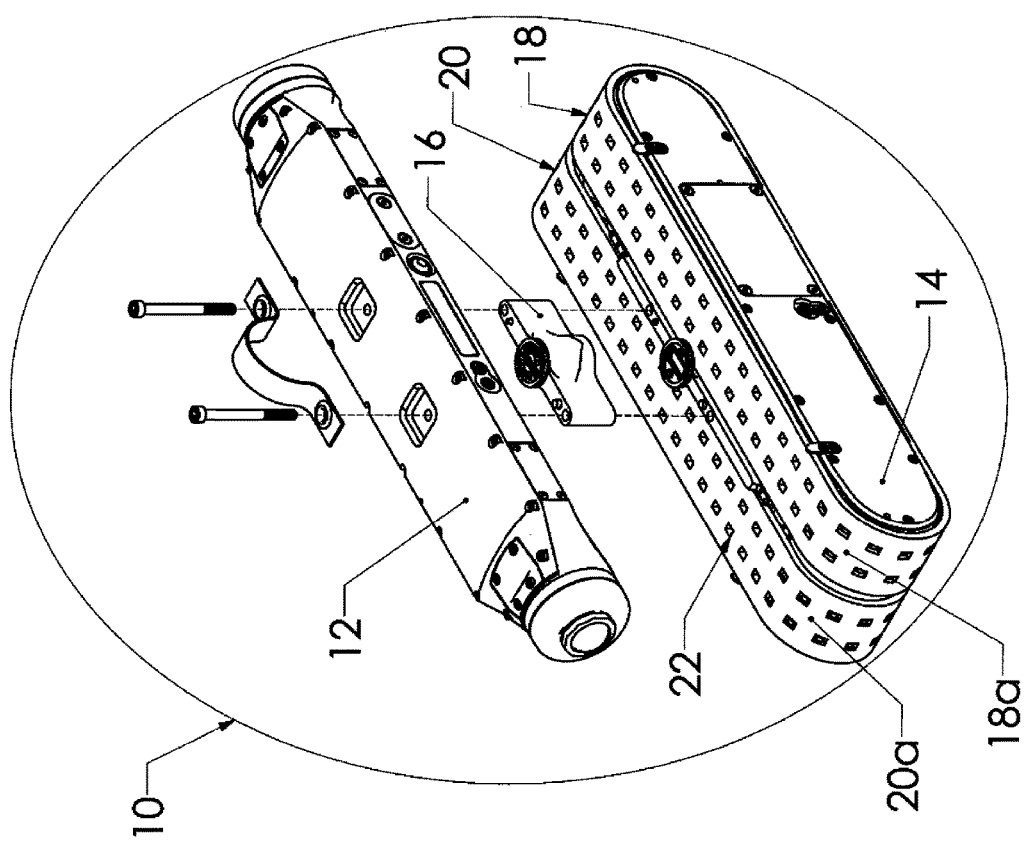
FIG. 1 illustrates an example pipe inspection robot.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "embodiment(s)" (or the like) means that a particular feature, structure, or characteristic described in connection with the embodiment is included in at least one embodiment. Thus, appearances of the phrases "according to embodiments" or "an embodiment" (or the like) in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Over time, issues may arise in various pipe segments. For example, different types of sediment deposits may accumulate in pipes, which may impede the flow of the materials. Additionally, the pipes may experience various other forms of damage such as cracks or corrosion, unauthorized inflows, etc. For these reasons, the pipes need to be routinely inspected and properly maintained.

One current inspection method involves inspectors visually identifying a deposit, for example by reviewing video captured by a pipe inspection robot or CCTV system. Through years of experience, inspectors are able to differentiate between different types of caustic substances (e.g., grease, calcium, iron oxide deposits, etc.). In this way, an experienced inspector may be able to distinguish between various types of inflows, various types of deposits or buildups, etc. However, this is more of an art than a science, with no metrics or rules except in the case of obvious substances, e.g., iron deposits tend to be red in color. An alternate solution is to take a sample of the deposit and bring it to a lab where tests can be conducted to determine the identity of the substance, e.g. with a spectrophotometer. However, this takes time and may not be ideal when a situation is time-sensitive. These technical issues present problems for users in that accurately identifying damage or deposits, if possible, may be difficult, time-consuming and expensive.

Accordingly, an embodiment provides a method for providing real-time chemical analysis of deposits found in pipelines using image based spectroscopy. Using this method, physical inspection and analysis of samples is no longer necessary. Rather, an embodiment may provide a non-contact identification technique that includes emitting a beam of terahertz (THz) radiation onto an object and receiving not only visual and topographic information, but also information related to the chemical composition of the object. Additionally, the THz radiation is slightly penetrative, so an embodiment may also provide depth information, e.g., image based information about an object in a first layer and an object in a second, deeper layer.

In an embodiment, other spectral imaging techniques may be utilized alone or in combination with a THz based technique. For example, an embodiment may couple THz spectral data with other spectral data, such as IR spectral data and/or UV spectral data, in addition to THz spectral data, for chemical analysis. Appropriate transmission and receiving components may therefore be included on-board a pipe inspection robot.

The description now turns to the figures. The illustrated example embodiments will be best understood by reference to the figures. The following description is intended only by way of example, and simply illustrates certain example embodiments.

FIG. 1 illustrates an example pipe inspection robot 10 that may be utilized for capturing pipe inspection data, including THz imaging data. For purposes of clarity, a partially exploded view of the pipe inspection robot 10 is shown in FIG. 1. As explained in more detail hereinafter, the device may be utilized to navigate, explore, map, etc., various environments (e.g., water pipes, sewer pipes, etc.). In an embodiment, the pipe inspection robot 10 may be implemented as an autonomous mobile robot 10 utilized for pipe inspection (e.g., a sewer pipe). However, it will be appreciated that the pipe inspection robot 10 may be embodied in any number of different types of inspection platforms, including non-autonomous devices and platforms, and may be utilized in a plurality of other environments.

The autonomous mobile robot 10 used by way of example for descriptive purposes includes a sensor component 12 and a chassis portion 14. The sensor component 12 is electrically and mechanically connected to the chassis portion 14. As shown in FIG. 1, the autonomous mobile robot 10 may also include a riser portion 16 which is positioned between the sensor component 12 and the chassis portion 14, and is electrically and mechanically connected to each. The riser portion 16 operates to increase the distance the sensor component 12 is situated above the lowest portion of the pipe, and may be utilized in large pipe applications to provide a desired vantage point for various sensing devices of the sensor component 12. Additionally, riser portion 16 and sensor component 12 are modular, i.e., they may be coupled/decoupled to and from the autonomous mobile robot 10. For example, according to other embodiments, the autonomous mobile robot 10 does not include the above-described riser portion 16. Functionality of the autonomous mobile robot 10 may be implemented by a computing device and/or a computer program stored on a computer-readable medium, as further described herein.

According to an embodiment, the sensor component 12 includes a plurality of sensing devices (e.g., a THz source, a camera, a radar device, a sonar device, an infrared device, a laser device, etc.) for sensing the conditions within the environment, a computing device communicably connected to the sensing devices and having a processor for processing raw information captured by the sensing devices, a memory device communicably connected to a computing device for storing the raw and/or processed information, and control circuitry communicably connected to the computing device for controlling various components of the autonomous mobile robot 10. The memory device may also be utilized to store software which is utilized by the autonomous mobile robot 10 to navigate, explore, map, etc., the environment.

The THz source of the sensor component 12 may be implemented using a variety of techniques. For example, an antenna or laser (beam pump) may act to produce a THz source that is directed to a pipe wall. In an embodiment, sensor component 12 includes an antenna or sensor such as a charged coupled device (CCD)/camera may receive reflections and/or transmissions of a THz source. The sensor component 12 is therefore capable of performing THz imaging data collection using an active transmission technique to paint an object such as a wall area of a pipe segment. In another embodiment, the sensor portion 12 may include a passive THz imaging element, which views the naturally occurring radiation of an object.

As further shown in FIG. 1, the chassis portion 14 includes a first track 18, and a second track 20. In an embodiment, the first track 18 is identical to the second track 20. The first and second tracks 18, 20 may be fabricated from any suitable material or combination of materials. The first and second tracks 18, 20 each define a plurality of openings 22 there-through. The openings 22 may be of any suitable shape and size, and may be arranged in any suitable configuration. Although only two rows of the openings 22 are shown in FIG. 1 for each track, it is understood that the openings 22 may be arranged in any number of rows. The first track 18 is positioned adjacent the second track 20. Collectively, the first and second tracks 18, 20 define a spacing there-between, and cover substantially the entire width of the chassis portion 14. For example, according to an embodiment, the width of the chassis portion is approximately 100 millimeters, and the first and second tracks 18, 20 collectively cover approximately 92 of the 100 millimeters.

The first track 18 defines a first surface 18a and a second surface (not shown in FIG. 1) opposite the first surface 18a. According an embodiment, the first surface 18a is the surface which comes in contact with an interior surface of a pipe when the autonomous mobile robot 10 is being utilized for a pipe application. The first surface 18a of the first track 18 is substantially smooth. Similarly, the second track 20 defines a first surface 20a and a second surface (not shown in FIG. 1) opposite the first surface 20a. The first surface 20a is the surface which comes in contact with an interior surface of a pipe when the autonomous mobile robot 10 is being utilized for a pipe application. Again, the first surface 20a of the first track 20 may be substantially smooth. The respective first surfaces 18a, 20a of the first and second tracks 18, 20 have a relatively high static coefficient of friction.

The first and second tracks 18, 20 may be referred to as full coverage/wide tracks. Due to the collective width of the first and second tracks 18, 20 relative to the width of the chassis portion 14, the first and second tracks 18, 20 collectively form nearly the entire "front," "bottom" and "rear" surfaces of the chassis portion 14. Thus, when the autonomous mobile robot 10 encounters any debris or feature within the sewer pipe, the first surfaces 18a, 20a of the first and second tracks 18, 20 come in contact with the debris or feature. In contrast to wheeled robots and narrow track robots, the full coverage/wide tracks 18, 20 are configured to enable the autonomous mobile robot 10 to climb over the debris or feature and continue performing the inspection, navigation, mapping, etc. Additionally, nearly all of the weight of the autonomous mobile robot 10 passes through the moving full coverage/wide tracks 18, 20 to the encountered debris or feature. Therefore, the autonomous mobile robot 10 is configured to always continue driving as the full coverage tracks 18, 20 cannot rotate without contacting something to react with and continue driving.

Figure 2:
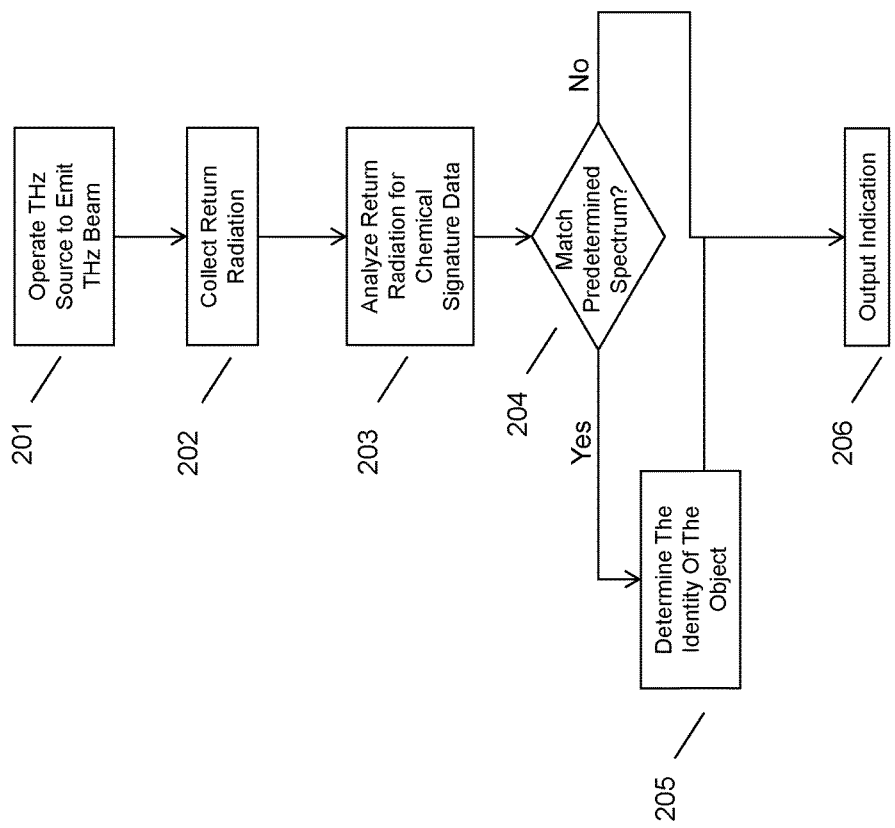
FIG. 2 illustrates an example method of using terahertz (THz) data to identify target objects.

Referring now to FIG. 2, at 201 an embodiment may operate a THz source to emit a THz beam to paint a target, e.g., wall of a pipe segment. This permits the collection of return radiation (THz beam) at 202. The return beam collected at 202 may comprise absorption and/or emission data related to chemical bonds of a target object, which may be resolved for example utilizing spectroscopy processing techniques.

The return data may comprise one or more characteristic absorption peaks, as sensed for example by sensor component 12 of FIG. 1, which permits analysis of the chemical composition of the pipe wall segment, as illustrated at 203. For example, THz spectroscopy utilizes wavelengths of radiation in the terahertz band, which ranges from about 1 mm to about 0.1 mm, to distinguish between various chemicals contained in an object according to their spectral characteristics. For example, a THz sensor may be used to emit a THz beam (that may be focused on a target object using a mirror or other optical structure) and sense return radiation that is influence by chemical(s) in a target object. The return radiation may therefore include information related to absorption spectra. In turn, various materials may be distinguished on the basis of their chemical compositions, e.g., in terms of classifying the materials based on dominant features contained within the spectral data related to certain chemical bonds of known materials. For example, in an embodiment, classification of the absorption spectra of a target object may be achieved by using a minimum distance classifier and neural network methods. By way of specific example, spectral data for a known material may be utilized as a reference for identifying a target object by comparison of one or more peaks in the target object's THz return data. THz images of a target object may be formed by integrating the peak data around one or more known frequencies in the THz band, e.g., 0.82 THz.

In an embodiment, a variety of THz laser sensing chips may be utilized for sensing or receiving the return radiation, e.g., provided within sensor component 12. Different chips have different strengths and weaknesses in terms of the environments they work in. In an embodiment, chips that are sensitive to different chemicals (e.g., bond vibrations) can be interchanged with chips in existing THz sensors to suit desired applications. For example, some chips may not work well when detecting reflections off of fabrics because there is a greater signal to noise ratio. However, those same chips may work very well with objects that are dark colored, e.g., an asbestos lined pipe that is pitch black may require a very different sensor than a sensor used in a typical pipe. In an embodiment, the THz beam generator and THz sensor may be utilized in air-filled pipes as well as pipes that are submerged with water.

THz imagery provides distinct advantages over other types of visual imagery, particularly in a pipe inspection implementation. For example, when a wave of visible light is directed onto an object, the light is reflected or refracted back and information relating to color, shape, and topography is received. When a beam of THz radiation is emitted, not only is return information about shape and topography received, but because each type of chemical bond has a unique vibrational frequency, THz spectroscopy leverages these differences in order to determine the chemical composition of an object based on the identification of its chemical bonds.

For example, as outlined at 203 and 204 of FIG. 2, an embodiment may analyze return radiation to produce peak data, e.g., in the form of an absorption/emission spectra, for a particular target, as shown at 203. The absorption/emission spectra may be used to identify one or more predetermined spectra, e.g., known spectra of cement, metal or metal alloys, rust, soil or organic material of varying types, etc., as shown at 204.

If a match is determined at 205, e.g., return radiation produces a spectra having one or more peaks matching (classified to a predetermined confidence level) to iron oxide, an embodiment may output an indication that a match for a particular chemical composition has been identified at 206. Otherwise, an embodiment may output an indication that no match has been found. In an embodiment, visual image data or additional imaging data may be collected by at least one camera or other sensing device mounted to autonomous mobile robot 10, e.g., including in sensor component 12. An embodiment may thus additionally capture visual data (images, video) such that a THz analysis may be improved (e.g., in terms of confidence) or omitted, e.g., if THz data is unresolvable, in favor of other or additional sensed data.

In addition to providing chemical information, THz radiation is also slightly penetrative. Some frequencies of THz radiation can penetrate several millimeters below the surface of a targeted object. This aspect of the radiation not only provides chemical information about the targeted object, but it also provides chemical information about what the targeted object may be laying on top of or layered over. For example, if part of a pipe appears to be corroded with rust, lime or other deposit, THz imaging may reveal that the corroded segment is composed of the components of cement, e.g., lime, carbonate, iron oxide, etc. If the THz imaging produces readings of chemical signatures that are suggestive of soil, because the original beam was directed at the pipe wall, this provides a strong indication that the pipe wall has become very thin and is in danger of failing or has in fact failed.

In an embodiment, a THz beam generator and a THz sensor (e.g., CCD/camera, crystal, etc.) may be mounted to autonomous mobile robot 10. In an embodiment, a THz beam generator and a THz sensor may be mounted to any type of robot that is able to capably traverse through a pipeline. In an embodiment, the THz beam generator and sensor may be mounted at different locations on the mobile inspection robot. For example, in order to attain 360-degree scanning ability, THz-related units may be positioned in an array, e.g., at the 3, 6, 9, and 12 o'clock locations of the sensor component 12. In an embodiment, power supplied to the THz units may be supplied by the autonomous mobile robot 10, may be supplied by a separate, dedicated battery, or may be supplied by a commercial power source (e.g., a wireline provided from the surface to the robot). In an embodiment, THz imaging may be conducted at-will, e.g., by a user-generated command, or may be set to scan continuously or intermittently, e.g., according to a program or a policy.

The processing at 203 and/or 204 may take place locally on the autonomous mobile robot 10 or may take place off-site on another information handling device (PC computer, laptop, tablet, etc.). In an embodiment, the processing may be completed in real-time or near real-time. For example, if THz imaging is being continuously run, the processing of each subsequent scan may lag behind by a few seconds because the previous scans need to be completed first.

An analysis of the collected THz data at 203 may be combined with other techniques. For example, a THz scan of an object may be conducted that collects chemical composition data for a pattern-matching algorithm that analyses spectral peak data to determine what the object actually is, e.g., based on comparison matching, as indicated at 204. In addition, a visual camera (or other imaging device) may be used to collect visual image data of the same target. Thus, in addition to comparing THz data to a database of known materials, an embodiment may couple this to a visual light analysis of the target object in order to refine or rank various possibilities of object identifications. For example, a suggested list of the top three most likely candidates of what the targeted object might be may be included in the output indication at 206.

Accordingly, images produced by THz imaging data (or data derived therefrom) may be overlaid or combined with traditional visual images or other data (e.g., pipe map data) using standard image alignment techniques. The benefits of this overlay are that a user not only obtains a visual of the internals of a pipe, but they also receive a metric as to what they are visualizing chemically.

An embodiment may relate the THz imaging data to various parts of a pipe network using pipe mapping data. For example, if a detailed mapping is available for a pipe network, the THz imaging data may be associated with the various parts of the pipe network. This permits a user to review visual inspection data for a particular part of the pipe network as well as related THz imaging data for the particular part of the pipe network.

Figure 3:
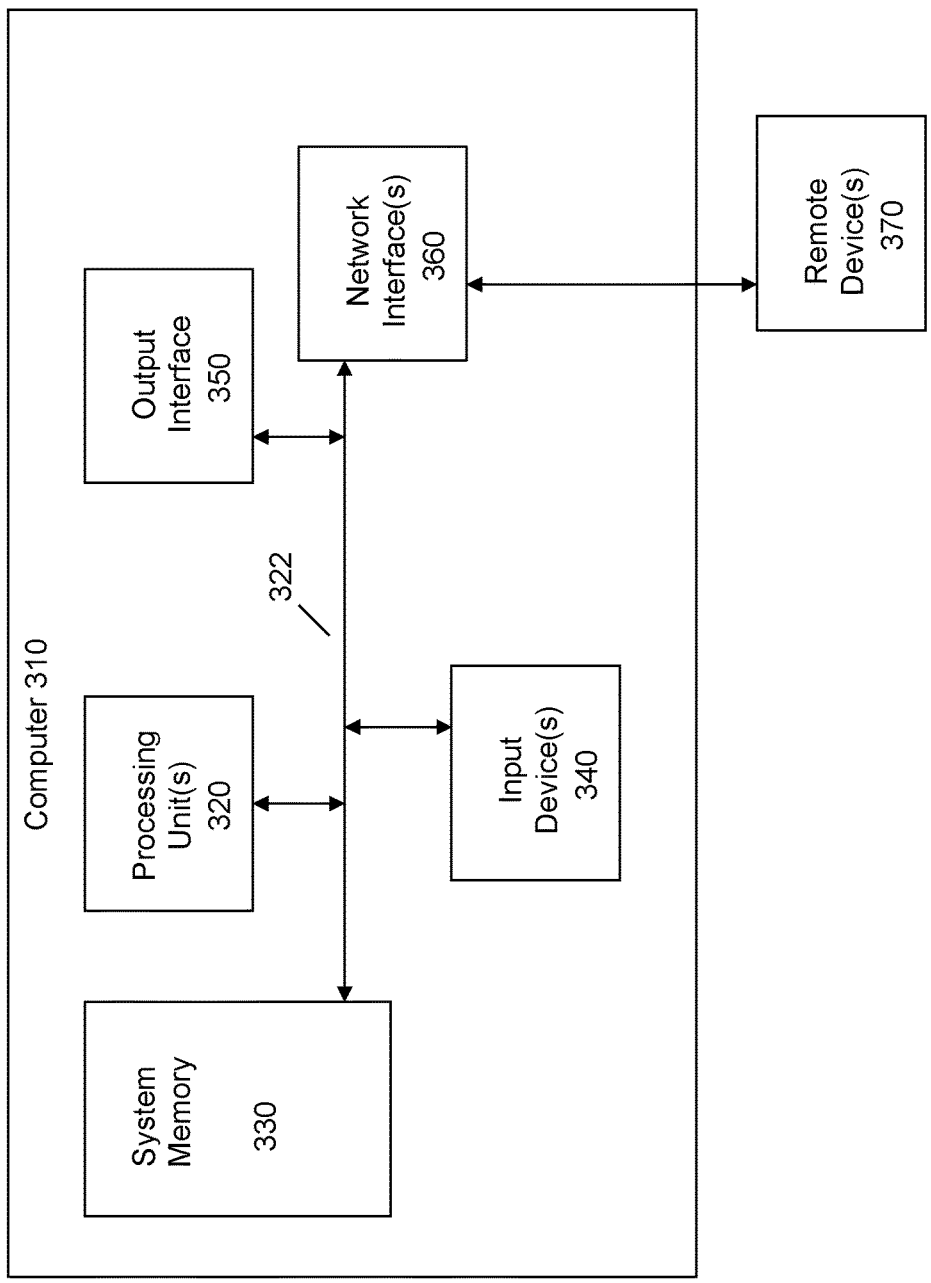
FIG. 3 illustrates an example of device electronics in the form of a computer.

It will be readily understood that certain embodiments can be implemented using any of a wide variety of devices or combinations of devices. Referring to FIG. 3, an example device that may be used in implementing one or more embodiments includes a computing device (computer) 310. In this regard, a computing device 310 may be operatively coupled to autonomous mobile robot 10 and provide hosted services (data storage, data analysis, data summary and querying, and the like). For example, computing device 310 may provide network based access to autonomous mobile robot 10 for reporting THz data, receiving data such as autonomous mission protocols, etc. Additionally or alternatively, autonomous mobile robot 10 may incorporate a computing device such as outlined in FIG. 3, e.g., included on board in sensor component 12.

The computing device 310 may execute program instructions configured to store an analyze pipe segment data and perform other functionality of the embodiments, as described herein. Components of the computing device 310 may include, but are not limited to, a processing unit 320, a system memory 330, and a system bus 322 that couples various system components including the system memory 330 to the processing unit 320. The computer 310 may include or have access to a variety of computer readable media, for example for storing infrastructure data indices. The system memory 330 may include computer readable storage media in the form of volatile and/or nonvolatile memory such as read only memory (ROM) and/or random access memory (RAM). By way of example, and not limitation, system memory 330 may also include an operating system, application programs, other program modules, and program data.

A user can interface with (for example, enter commands and information) the computing device 310 through input devices. A monitor or other type of device can also be connected to the system bus 322 via an interface, such as an output interface 350. In addition to a monitor, computers may also include other peripheral output devices. The computing device 310 may operate in a networked or distributed environment using logical connections to one or more other remote computers or databases, e.g., autonomous mobile robot 10. The logical connections may include a network, such local area network (LAN) or a wide area network (WAN), but may also include other networks/buses.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device to produce a special purpose machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A pipe inspection robot, comprising:
a powered track system providing movement to the pipe inspection robot to traverse through the interior of a water or sewer pipe;
a sensor component attached to the powered track system; and
a processor;
said sensor component comprising: a terahertz (THz) beam source, a receiver; and a visual camera;
said processor configured to:
operate the sensor component to collect THz data and visual image data related to an interior surface of the water or sewer pipe as the pipe inspection robot traverses through the water or sewer pipe;
associate the THz data with visual image data; and
communicate the THz data and the visual image data collected over a network connection.

2. The pipe inspection robot of claim 1, wherein the THz data comprises spectral data.

3. The pipe inspection robot of claim 2, wherein the spectral data comprises one or more peaks.

4. The pipe inspection robot of claim 1, wherein the processor is further configured to identify one or more peaks in the THz data.

5. The pipe inspection robot of claim 4, wherein the processor is further configured to compare the one or more peaks to one or more known spectra for a predetermined set of water or sewer pipe interior wall materials.

6. The pipe inspection robot of claim 5, wherein the processor is further configured to compare the one or more peaks to one or more known spectral peaks using a neural network.

7. The pipe inspection robot of claim 5, wherein:
the THz beam source directs a THz beam to a target object of the pipe wall; and
the processor is further configured to identify the target object.

8. The pipe inspection robot of claim 1, wherein the THz source comprises a laser.

9. The pipe inspection robot of claim 1, wherein the receiver comprises a charge-coupled device.

10. A method for identifying a target object of a pipe wall, comprising:
positioning a pipe inspection robot within a water or sewer pipe to traverse through the interior of the water or sewer pipe;
receiving, using a visual camera of the pipe inspection robot, visual image data related to an interior surface of the water or sewer pipe as the pipe inspection robot traverses through the water or sewer pipe;
emitting, using a terahertz (THz) beam source of the pipe inspection robot, a laser beam towards a target object of the interior surface of the water or sewer pipe;
receiving, using a THz receiver of the pipe inspection robot, THz data related to the target object as the pipe inspection robot traverses through the water or sewer pipe;
associating, using a processor, the THz data with the visual image data and pipe network mapping data;
analyzing, using a processor, the THz data;
determining, based on the analyzing, an identity of the target object; and
providing the identity of the target object in a visual display comprising one or more of the pipe network data, a visual image, and a THz image.

11. The method of claim 10, wherein the THz data comprises spectral data.

12. The method of claim 10, wherein the spectral data comprises one or more peaks.

13. The method of claim 12, wherein the determining comprises using the one or more peaks in the THz data.

14. The method of claim 13, wherein the one or more peaks are compared to one or more known spectra for a predetermined set of water or sewer pipe interior wall materials.

15. The method of claim 14, wherein the one or more peaks are compared to one or more known spectral peaks using a neural network.

16. The method of claim 14, wherein the emitting comprises directing the laser beam toward the target object of the pipe wall.

17. The method of claim 10, further comprising obtaining, using a sensor component of the pipe inspection robot, additional inspection data.

18. The method of claim 17, further comprising combining, using a processor, the additional inspection data with the THz data.

19. A method, comprising:
traversing, with a pipe inspection robot, through an interior of a water or sewer pipe;
receiving, using a visual camera of the pipe inspection robot, visual image data related to a target object of an interior surface of the water or sewer pipe;
receiving, using a THz receiver of the pipe inspection robot, THz data related to the target object;
associating, using a processor, the THz data with the visual image data;
analyzing, using a processor, the THz data;
determining, based on the analyzing, an identity of the target object; and
providing the identity of the target object in a visual display comprising the visual image data and the THz data.

20. The method of claim 19, comprising overlaying the THz data with visual image data in a combined image, wherein the combined image comprises THz data aligned with visual data of the target object in the combined image.

* * * * *